US009651571B2

(12) United States Patent
Sasaki et al.

(10) Patent No.: US 9,651,571 B2
(45) Date of Patent: May 16, 2017

(54) SPECIMEN PRE-PROCESSING CONNECTION DEVICE AND SYSTEM PROVIDED WITH DEVICE

(71) Applicant: HITACHI HIGH-TECHNOLOGIES CORPORATION, Tokyo (JP)

(72) Inventors: Takahiro Sasaki, Tokyo (JP); Masashi Akutsu, Tokyo (JP); Takeshi Matsuka, Tokyo (JP); Kuniaki Onizawa, Tokyo (JP); Naoto Tsujimura, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 15/030,452

(22) PCT Filed: Dec. 10, 2014

(86) PCT No.: PCT/JP2014/082608
§ 371 (c)(1),
(2) Date: Apr. 19, 2016

(87) PCT Pub. No.: WO2015/093354
PCT Pub. Date: Jun. 25, 2015

(65) Prior Publication Data
US 2016/0252539 A1 Sep. 1, 2016

(30) Foreign Application Priority Data
Dec. 19, 2013 (JP) .................................. 2013-261954

(51) Int. Cl.
*G06F 7/00* (2006.01)
*G01N 35/04* (2006.01)

(52) U.S. Cl.
CPC ..... *G01N 35/04* (2013.01); *G01N 2035/0406* (2013.01); *G01N 2035/0412* (2013.01)

(58) Field of Classification Search
None
See application file for complete search history.

(56) References Cited

U.S. PATENT DOCUMENTS 5,623,415 A * 4/1997 O'Bryan ............ G01N 35/021
198/617
2002/0015665 A1 2/2002 Lindsey et al.
(Continued)

FOREIGN PATENT DOCUMENTS

JP 11-500224 A 1/1999
JP 2000-266761 A 9/2000
(Continued)

OTHER PUBLICATIONS

International Search Report of PCT/JP2014/082608 dated Mar. 17, 2015.

*Primary Examiner* — Yolanda Cumbess
(74) *Attorney, Agent, or Firm* — Mattingly & Malur, PC

(57) ABSTRACT

The present invention addresses the problem of inefficient utilization in a specimen pre-processing connection system due to integrated operation of a portion for connecting with pre-processing and a portion for connecting with an automated analysis system. The specific structure of the present invention contributes to providing a highly efficient system by causing a function for connecting to pre-processing and receiving a specimen from a pre-processing system and a function for connecting to an automated analysis system and transferring a specimen to the automated analysis system to each operate independently in a single unit, so that the functions do not affect each other during reset processing, and making it possible for either function to operate alone.

11 Claims, 8 Drawing Sheets

(56) References Cited

U.S. PATENT DOCUMENTS

| | | |
|---|---|---|
| 2012/0174687 A1 | 7/2012 | Ohga et al. |
| 2012/0177547 A1 | 7/2012 | Fukugaki et al. |
| 2013/0117042 A1 | 5/2013 | Tajima et al. |
| 2013/0281279 A1* | 10/2013 | Yagi ................. B04B 9/146 494/1 |
| 2014/0208872 A1* | 7/2014 | Yasuzawa ............ G01N 35/04 73/863.01 |

FOREIGN PATENT DOCUMENTS

| | | |
|---|---|---|
| JP | 2003-066050 A | 3/2003 |
| JP | 2004-505249 A | 2/2004 |
| JP | 2005-156196 A | 6/2005 |
| JP | 2012-184977 A | 9/2012 |
| WO | 2011/040197 A1 | 4/2011 |
| WO | 2011/040203 A1 | 4/2011 |
| WO | 2011/142182 A1 | 11/2011 |
| WO | 2013/042549 A1 | 3/2013 |

* cited by examiner

Fig. 7A
(a)
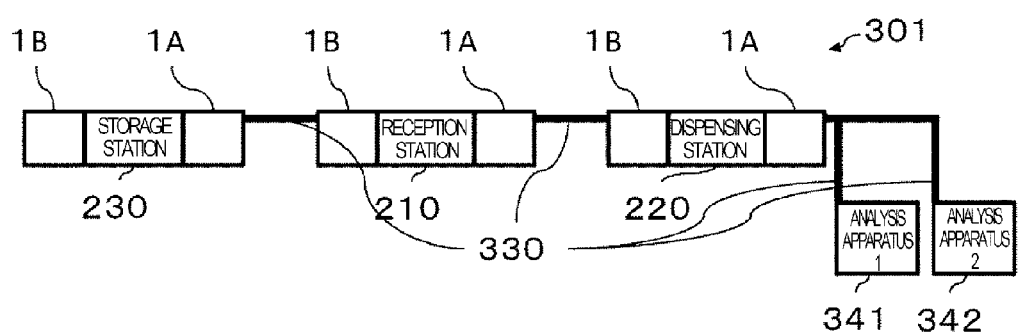
(b)
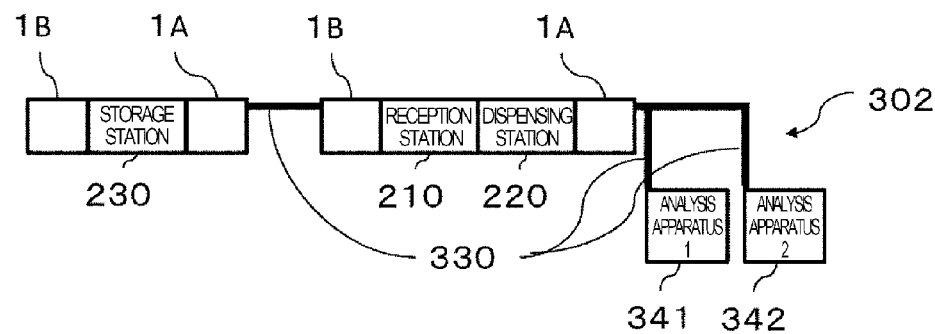

Fig. 7B
(c)
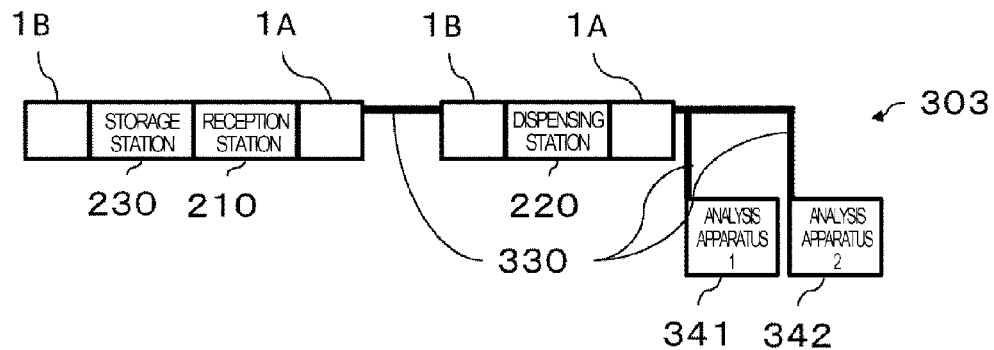
(d)
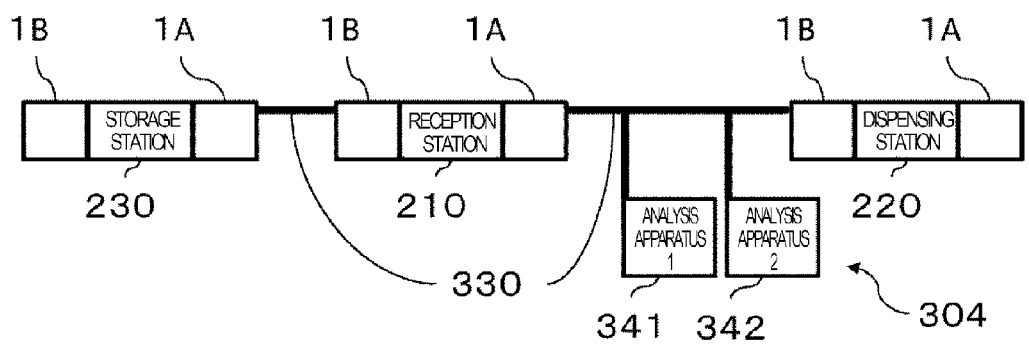

SPECIMEN PRE-PROCESSING CONNECTION DEVICE AND SYSTEM PROVIDED WITH DEVICE

TECHNICAL FIELD

The present invention relates to a specimen pre-processing connection apparatus that connects a specimen pre-processing automation system automatically performing the pre-processing of a specimen and a transport system (hereinafter, an automatic analysis system) including an automatic analysis apparatus automatically analyzing components of a specimen and transports a specimen between these systems, and a system including the specimen pre-processing connection apparatus.

BACKGROUND ART

In recent years, in an inspection room of a hospital, the automation of manual labor in inspection work has been advanced for the purpose of improving work efficiency and preventing the mix-up of a specimen and the infection of a worker. In order to introduce an automatic analysis apparatus and to realize pre-processing (centrifugation, an unplugging process, a dispensing process, and the like) and post-processing (a plugging process, the storage of a specimen, and the like) which occupy the majority of an inspection work time, and the automation of a specimen analysis process, a system related to the pre-processing and transportation of a specimen (hereinafter, a specimen transport system) has been invented and released in the market.

In general, a specimen transport system has a structure in which a specimen processing system performing the pre-processing and post-processing of a specimen and an analysis system analyzing a specimen are connected to each other by a transport unit. In the specimen processing system, a plurality of units having various functions are disposed along the transport line. In general, the specimen processing system is configured such that a specimen is injected from an injection unit which is disposed upstream of the transport line, the specimen is processed in the units disposed along the transport line, and the processed specimen is stored in a storage unit on the most downstream side. Meanwhile, the specimen processing system may be divided into systems different from each other during a pre-processing process and a post-processing process, and the specimen processing system and the analysis system may be directly connected to each other.

For example, PTL 1 discloses a system in which a dispensing unit is disposed at the end thereof, a transport line which moves backward against a transport line from an injection unit to the dispensing unit is provided, and a specimen processed and stored in the dispensing unit is transported in an upstream direction by the transport line moving backward.

CITATION LIST

Patent Literature

PTL 1: International Publication No. WO 2011/040203

SUMMARY OF INVENTION

Technical Problem

Incidentally, it is considered that a specimen processing system and an analysis system cannot be used individually. For example, such a state includes a case where consumables are required to be added to some units of the specimen processing system, a case where the shortage of a reagent occurs in the analysis system, or a case where the maintenance of each system is performed. Furthermore, units operated during the day and the night may be used interchangeably in an inspection room, and thus it is considered that all of the systems are not in an operation state. In this case, in the specimen transport system disclosed in PTL 1, a transport path on the specimen processing system side is required to be in a closed loop state so that a process of transporting a specimen can be completed only within the specimen processing system, in order to stably operate the specimen processing system regardless of the state of the analysis system. On contrary, in order to perform an operation using only the analysis system in a case where the specimen processing system cannot be used, a transport path on the analysis system side is required to be set to be in a closed loop state.

Accordingly, a transport path of a unit disposed at an end of the specimen processing system or the specimen processing system has to be set to be in a closed loop state. However, a unit disposed at an end of a pre-processing system varies depending on a configuration (layout) of the pre-processing system. For this reason, when a transport path of a unit disposed at an end is designed to have a closed loop structure for each system layout, there is a problem that structures of the respective units cannot be unified and standardized.

Solution to Problem

In order to solve the above-mentioned problem, a connection unit according to claim 1 of the invention includes a first transport line that transports a specimen rack holding a specimen in a first direction, a second transport line that transports a specimen rack holding a specimen in a second direction opposite to the first direction, a first connection bypass that connects the first transport line and the second transport line to each other and transports a specimen rack holding a specimen in a third direction, and a second connection bypass that connects the first transport line and the second transport line to each other and transports a specimen rack holding a specimen in a fourth direction opposite to the third direction, and holds a specimen for forming a first loop structure by the first transport line, the second transport line, and the first connection bypass and forming a second loop structure by the first transport line, the second transport line, and the second connection bypass.

Advantageous Effects of Invention

According to the invention, one unit can have two functions as an end point of a specimen processing system connected to a specimen processing system and as a start point of an analysis system connected to an automatic analysis system.

In addition, according to the invention, it is easy to separately control an operation regarding connection to a pre-processing system and an operation regarding connection to an automatic analysis system, because of a simple structure. Thereby, it is possible to separately perform a reset process on a portion connected to the pre-processing system and a portion connected to the automatic analysis system without including a plurality of processing apparatuses CPU, and to perform an operation more efficiently by avoiding the stop of the overall system which cannot be avoided in a system that operates both the systems integrally.

Furthermore, control for stopping only any of functions (hereinafter, an off-line mode) is facilitated depending on circumstances of the automatic analysis system and the pre-processing system which are connected to the system, and thus it is possible to construct a system with higher flexibility.

BRIEF DESCRIPTION OF DRAWINGS

FIG. 7A is a diagram illustrating the concept of division arrangement of the pre-processing system according to the invention.

FIG. 7B is a diagram illustrating the concept of division arrangement of the pre-processing system according to the invention.

DESCRIPTION OF EMBODIMENTS

An outline of a representative invention among inventions described in the specification will be briefly described below.

Figure 1:
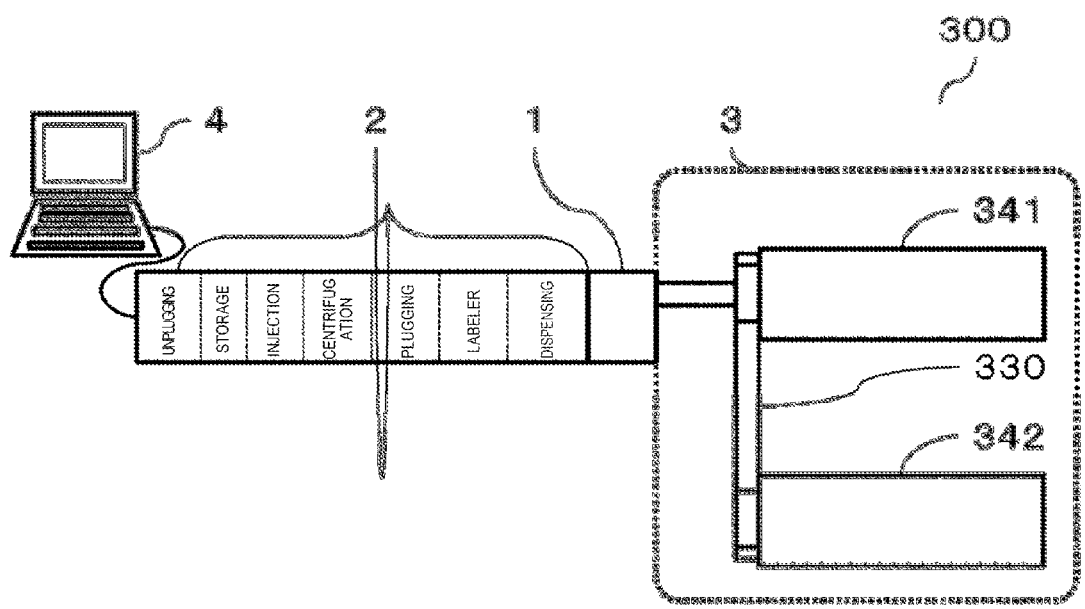
FIG. 1 is a diagram illustrating the overall configuration of a system according to the invention.
Figure 2:
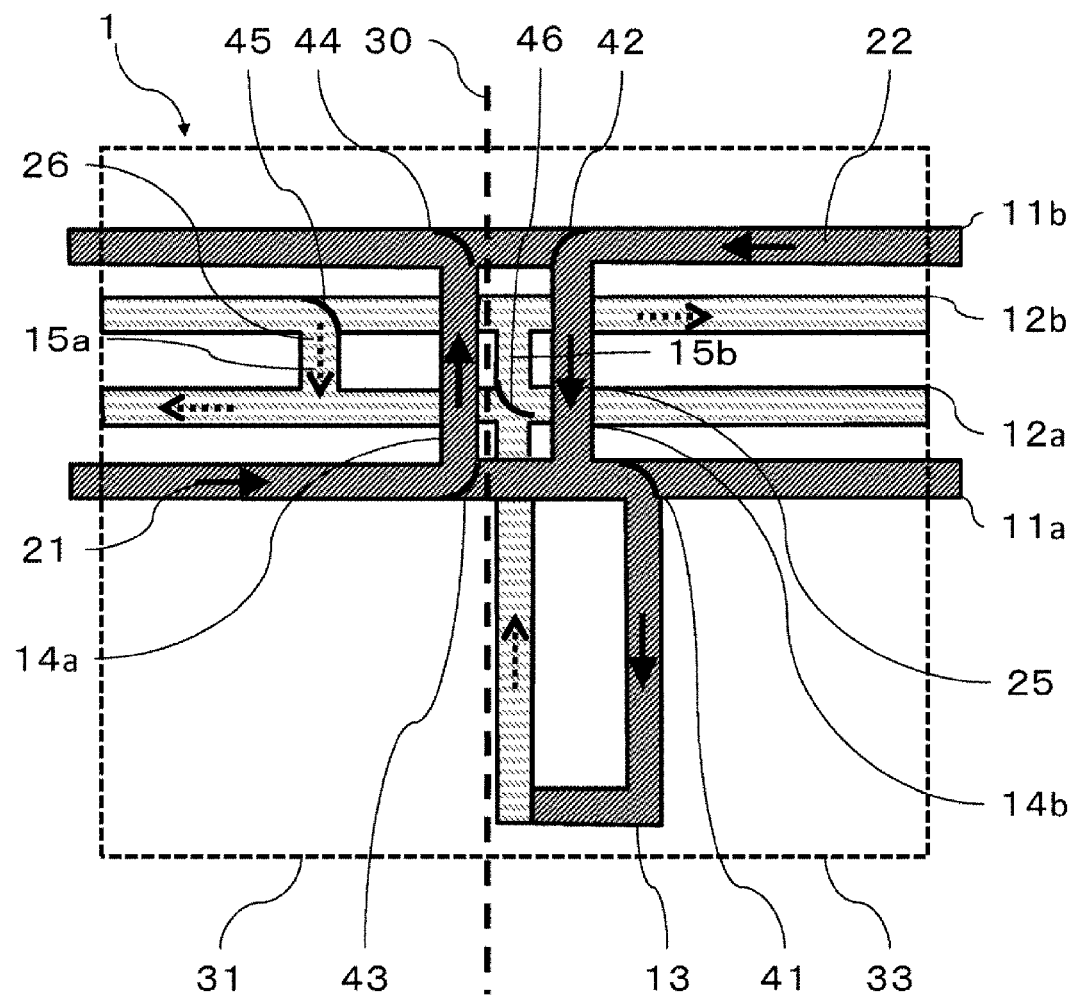
FIG. 2 is a schematic diagram illustrating a path configuration of a specimen pre-processing connection system according to the invention.
Figure 3:
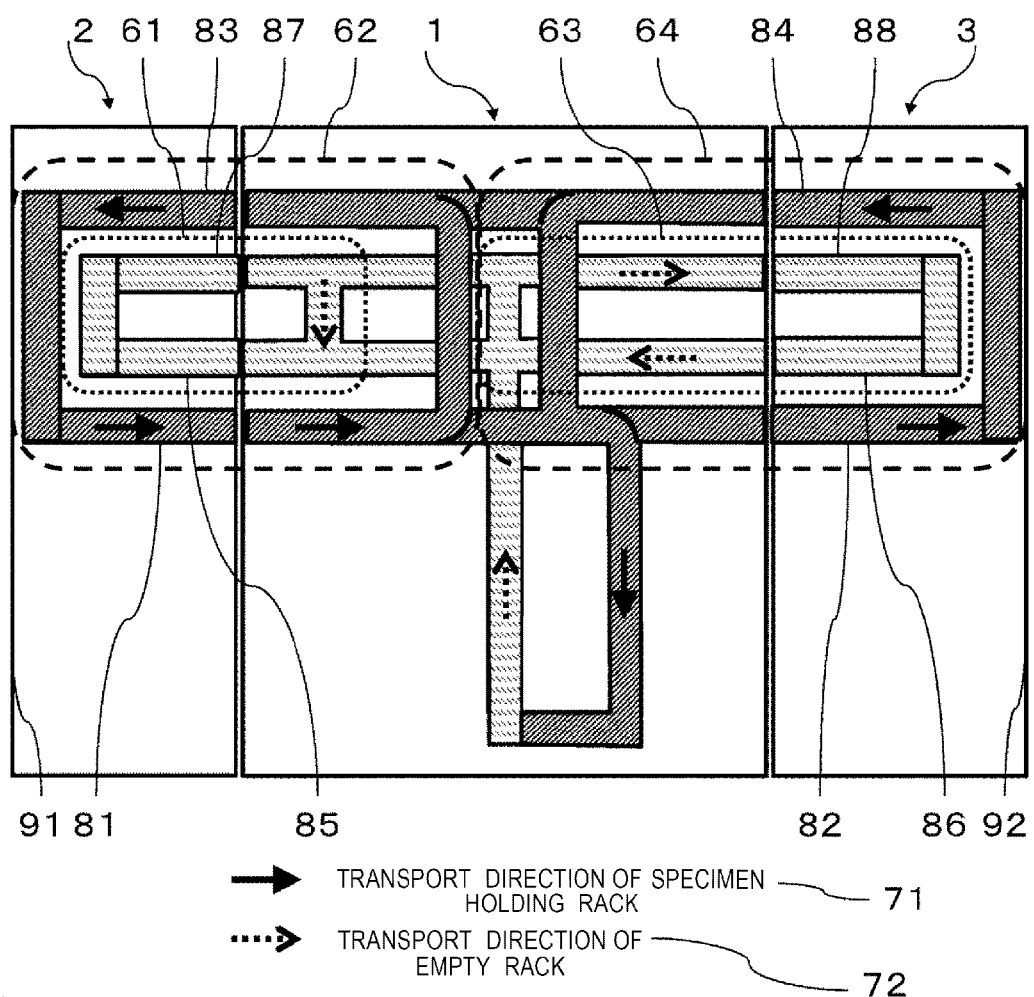
FIG. 3 is a schematic diagram illustrating connection of the specimen pre-processing connection system, a pre-processing system, and an automatic analysis system according to the invention.
Figure 4:
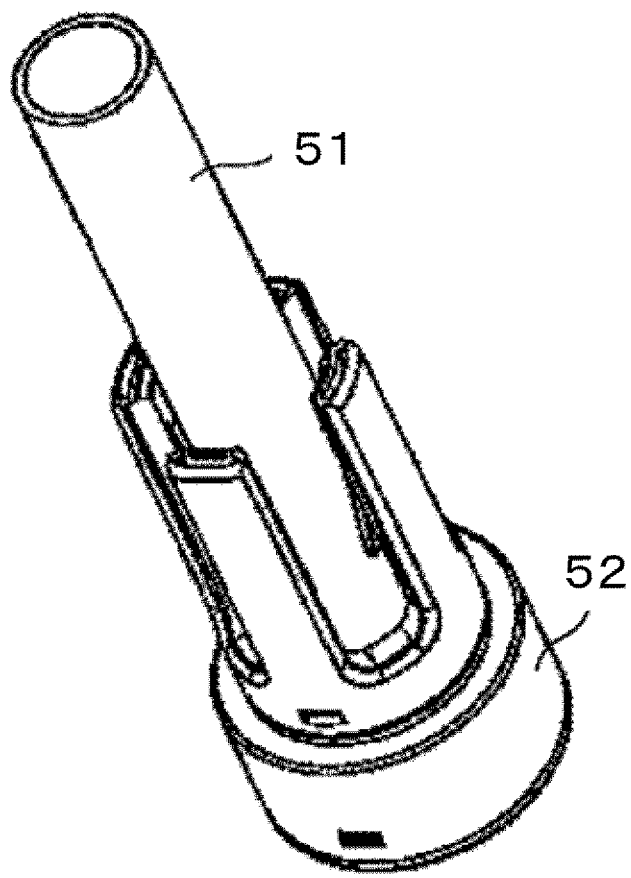
FIG. 4 is a diagram illustrating a specimen and a rack.
Figure 5:
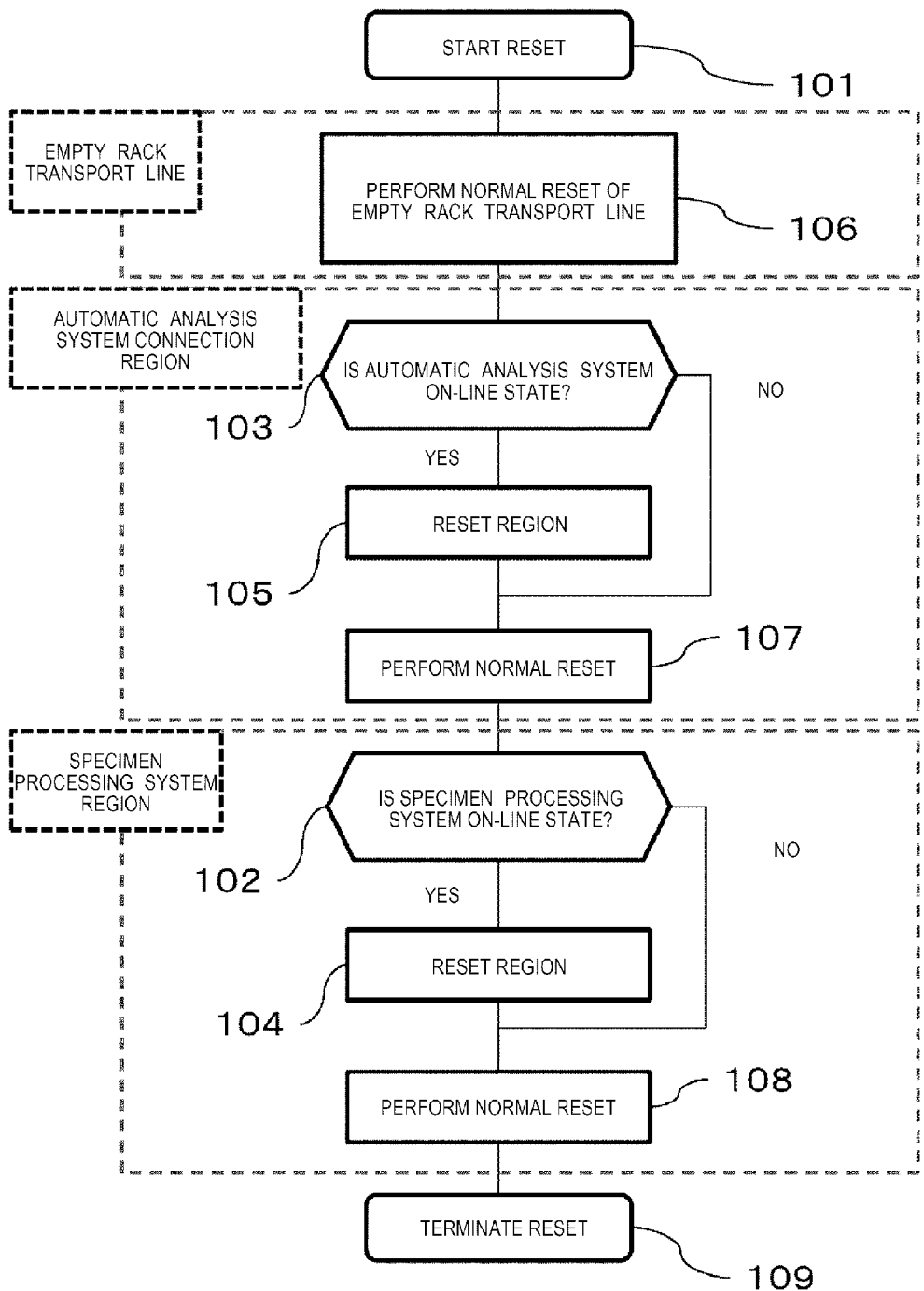
FIG. 5 is a flowchart illustrating a method of controlling a specimen pre-processing connection system according to the invention.
Figure 6:
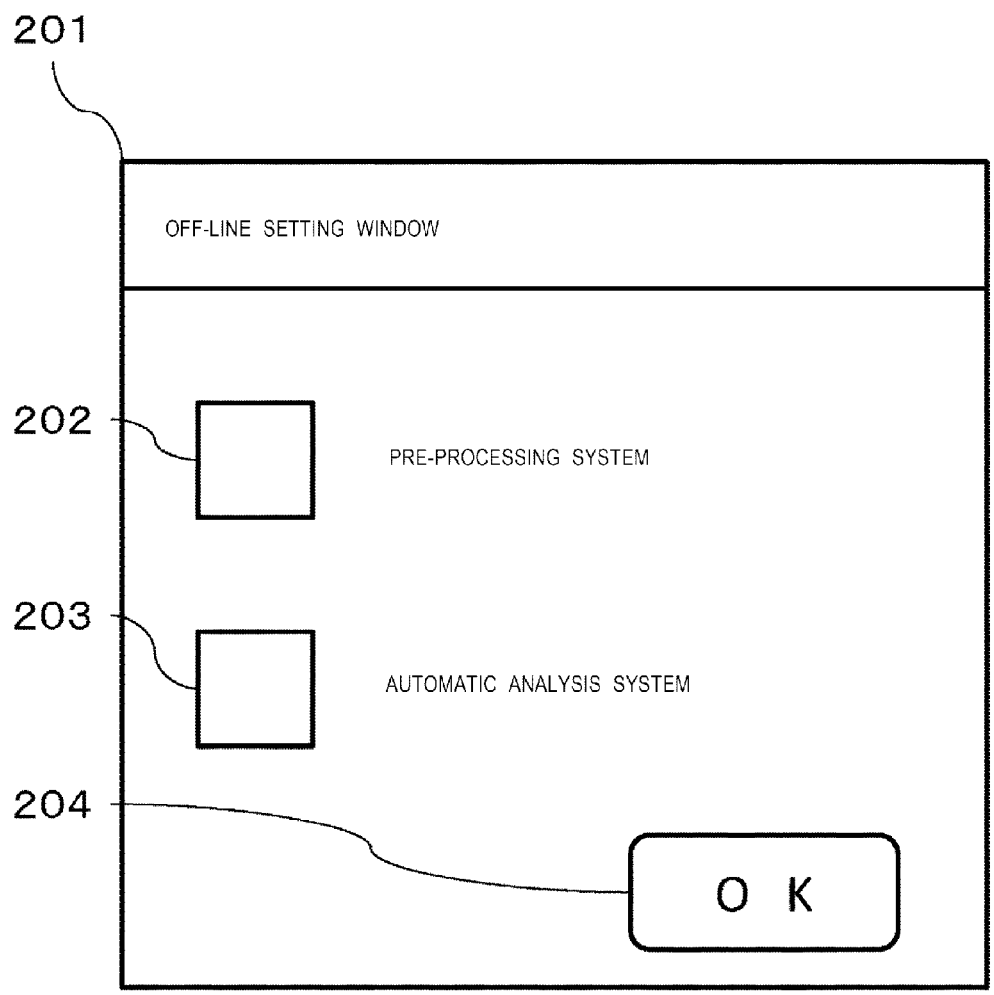
FIG. 6 is a diagram illustrating a setting screen related to off-line setting of the specimen pre-processing connection system according to the invention.

FIG. 1 is a diagram illustrating the overall configuration of a system according to the invention. FIG. 2 is a schematic diagram illustrating a path configuration of a connection unit according to the invention. FIG. 3 is a schematic diagram illustrating connection of the connection unit, a specimen processing system, and an automatic analysis system according to the invention. FIG. 4 is an example illustrating a specimen and a specimen rack. FIG. 5 is a flow chart illustrating a method of controlling a specimen pre-processing connection system according to the invention. FIG. 6 is a diagram illustrating a setting screen related to off-line setting of the specimen pre-processing connection system according to the invention.

The overall configuration of a system 300 will be described with reference to FIG. 1. The system 300 includes a pre-processing system 2, an automatic analysis system 3, a connection unit 1 that connects the systems to each other, and a control unit 4 (computer) which controls the systems and the unit. Here, the connection unit 1 is a main portion according to the invention.

The specimen processing system 2 refers to a system that, with respect to a specimen 51 obtained from a patient and then sent into an inspection room, performs processes represented as arrival confirmation, centrifugation, an unplugging process, a dispensing process, a plugging process, a storage process, and the like, that is, a series of processes required before the injection of the specimen into an automatic analysis apparatus. For example, the specimen processing system includes a plugging unit, a storage unit, an injection unit, a centrifugal unit, a labeler unit, and a dispensing unit. An arrangement order of the units may be changed depending on the size or layout of the system. In addition, other units may also be included depending on the purpose of processing.

On the other hand, the automatic analysis system 3 refers to a system that includes one or more automatic analysis apparatuses (341, 342) analyzing components of the specimen 51 and a line (330) transporting the specimen 51 to the automatic analysis apparatuses.

A configuration of the connection unit 1 will be described with reference to FIG. 2. The connection unit 1 includes main transport lines 11a and 11b that transport a specimen rack 52 holding the specimen 51, empty rack transport lines 12a and 12b that exclusively transport the empty rack 52, a connection line 13 that connects the main transport line and the empty-rack-only transport line to each other, main transport line connection bypasses 14a and 14b that connect the main transport lines to each other, and empty rack line connection bypasses 15a and 15b that connect the empty-rack-only transport lines to each other.

In order to avoid degradation of processing capacity due to a clog caused by transporting a rack having the specimen 51 installed thereon and an empty rack 52 on the same line, the empty rack transport line 12 is disposed separately from the main transport line 11 and is set as a line for exclusively transporting only an empty rack. In addition, in order to avoid an increase in the size of the system, it is preferable to dispose the empty rack transport line 12 at the lower position of the main transport line 11.

The connection line 13 is installed to connect the main transport line 11a and the empty rack transport line 12 to each other. In a case where the empty rack transport line 12 is disposed at the lower position of the main transport line 11, the connection line 13 is configured to be inclined to connect an upper line and a lower line to each other.

Next, a function of the connection unit 1 in an inspection room will be described with reference to FIG. 3. The left end of the connection unit 1 is connected to the specimen processing system 2, the right end thereof is connected to the automatic analysis system 3, and the left and right ends thereof function as units that transport the specimen 51 therebetween. Meanwhile, although the specimen processing system 2 and the automatic analysis system 3 are briefly described herein, a plurality of functional modules such as a specimen injection module, a centrifugation module, unplugging and plugging modules, a dispensing module, and a specimen storage module are configured to be connected to each other in the actual pre-processing system 2. In addition, the automatic analysis system 3 may be configured such that a plurality of analysis modules are connected to each other, and a plurality of automatic analysis systems 3 may be connected to each other.

More specifically, the main transport line 11a transporting a specimen from the specimen processing system 2 side to the analysis system 3 side is connected to a delivery line 81 which is an end point within the pre-processing system 2 at the left end thereof and is connected to a reception line 82 which is a start point within the automatic analysis system 3 at the right end thereof. The main transport line 11b transporting a specimen from the analysis system 3 side to the specimen processing system 2 side is connected to a reception line 83 within the specimen processing system 2 at the left end thereof and is connected to a delivery line 84 within the automatic analysis system 3 at the right end thereof. An empty rack transport line 12a transporting an empty rack from the analysis system 3 side to the specimen processing system 2 side is connected to an empty rack reception line 85 within the pre-processing system 2 at the left end thereof and is connected to an empty rack delivery line 86 within the automatic analysis system 3 at the right end thereof. An empty rack transport line 12b transporting an empty rack from the specimen processing system 2 side to the analysis system 3 side is connected to an empty rack delivery line 87 within the pre-processing system 2 at the left end thereof and is connected to an empty rack reception line 88 within the automatic analysis system 3 at the right end thereof.

Next, roles of lines and bypasses and a flow of a specimen 51 will be described with reference to FIGS. 2 and 3.

Among specimens 51 processed by the above-mentioned specimen processing system 2, a specimen 51 analyzed by the automatic analysis apparatus is transported to the main transport line 11a. The specimen 51 is transported in a direction of an arrow 21 on this line, and is sent to the automatic analysis system 3. A branch 41 connected to the empty rack transport line 12a is present on the line 11a, and thus a specimen 51 failed to be subjected to pre-processing or a specimen 51 having lost a path can be stopped to be transported to the automatic analysis system 3 by using the branch 41 and can be taken out on the connection line 13. In a case where the specimen 51 is removed, a rack is configured as the empty rack 52, and is recovered by the empty rack transport line 12a through the connection line 13.

The specimen 51 having returned from the automatic analysis system 3 is transported to the main transport line 11b. The specimen 51 is transported in a direction of an arrow 22 on the line, is sent back to the pre-processing system, and is subjected to a predetermined process, such as a storage process, in the pre-processing system. A branch 42 is also installed in the main transport line 11b. In a case where the specimen 51 required to be reexamined is returned, the course thereof can be changed to the main transport line connection bypass 14b (arrow 25) using the branch 42, and can be transported to the automatic analysis system 13 again through the main transport line 11a. Alternatively, a specimen 51 failed to be processed within the automatic analysis system is similarly transported in the order of the branch 42, the main transport line connection bypass 14b, the main transport line 11a, and the branch 41, and it is possible to remove the specimen 51 on the connection line 13 and to collect the empty rack 52.

The connection unit 1 plays a role in exchanging a specimen 51 between the specimen processing system 2 and the automatic analysis system 3 and a role in circulating the empty rack 52. In a case where the empty rack 52 is intensively transported to either the specimen processing system 2 or the automatic analysis system 3 and becomes exhausted, there is the possibility of an operation as a system being stopped. In order to avoid this, a function of supplying the empty rack 52 to both the systems is provided to a specimen pre-processing connection system, which is located at an intermediate position between the systems. Specifically, empty-rack-only transport lines form loop structures 61 and 63 within a region 31 connected to the pre-processing system 2 and a region 33 connected to the automatic analysis system 3, respectively.

The empty rack line connection bypass 15 and the connection line 13 play such a role. The former one transports a specimen 51 in a direction of arrow 26. The empty rack transport lines 12b and 12a connected to the empty rack lines 87 and 85 of the pre-processing system 2 form the loop structure 61. Similarly, regarding the latter one, the loop structure 63 is formed by the presence of the connection line 13.

In general, the empty rack 52 supplied from the empty rack line 87 of the pre-processing system 2 is returned to the empty rack line 85 of the pre-processing system 2 through the empty rack line connection bypass 15. Similarly, regarding the latter one, the empty rack 52 supplied from the empty rack line 86 of the automatic analysis system 3 is returned to the empty rack line 88 of the automatic analysis system 3 through the connection line 13.

Here, the empty rack 52 supplied from the empty rack line 87 of the specimen processing system 2 is transported to the empty rack line 88 of the automatic analysis system 3 through the empty-rack-only transport line (advancing) 12b as necessary. Similarly, the empty rack 52 supplied from the empty rack line 86 of the automatic analysis system is transported to the empty rack line 85 of the pre-processing system 2 through the empty-rack-only transport line (returning) 12a. Thereby, the mutual supply of the empty rack between both the systems is realized, and thus the empty rack is avoided being exhausted.

In addition, a rack holding a specimen 51 has to be circulated within the specimen processing system and the analysis system, and thus a main transport line transporting the rack having the specimen 51 installed thereon is also required to have a loop structure. In the invention, the main transport line connection bypass 14a in a pre-processing system region and the main transport line connection bypass 14b in an automatic analysis system region form loop structures 62 and 64, respectively.

In the invention, the connection unit 1 is conceptually divided into two regions. When one of the regions is set as a connection region (region 31 on the left side of a dashed line 30) to the specimen processing system 2, and the other is set as a connection region (region 33 on the right side of the dashed line 30) to the automatic analysis system, lines in the respective regions can form a total of two types of loop structures, that is, the loop structures 61 and 62 and the loop structures 63 and 64 together with the lines within the specimen processing system 2 and the automatic analysis system 3 as described above.

Next, the control of the connection unit 1 will be described.

As described above, the pre-processing system connection region 31 is configured as the right end of the pre-processing system 2, and the automatic analysis system connection region 33 is configured as the left end 3 of the automatic analysis system by the presence of the loop structures 61, 62, 63, and 64.

In the invention, respective regions are configured to be capable of being controlled separately. For example, in a reset process, a former one is the lowermost end and is set as a standard of the reset process, while a latter one is the uppermost end and can start reset by receiving an instruction from a downstream line. In addition, it is possible to perform an off-line process for stopping only one of the regions.

A specific workflow of an example of a reset process will be described below with reference to FIG. 5.

When the start of a reset process is instructed by the control unit 4 (step 101), the empty rack transport line 12, the automatic analysis system connection region 33, and the processing system connection region 31 start the reset process separately.

Regarding a mechanism, the empty rack transport line 12b, the empty rack transport line 12a, the empty rack line connection bypass 15, and the connection line 13 correspond to the empty rack transport line 12. Since these lines are capable of controlling reset regardless of the on-line and off-line states of the specimen processing system 2 and the automatic analysis system 3, normal reset is performed (step 106), and the reset process is terminated.

In the automatic analysis system connection region 33, a reset control method varies depending on whether the automatic analysis system 3 is in an on-line state or an off-line state. Meanwhile, the on-line state refers to a state where the automatic analysis system 3 is in operation, and the off-line state refers to a state where the automatic analysis system 3 is not in operation. A mechanism that receives or sends the rack 52 from the automatic analysis system 3 is not required to perform a reset operation in a case where the automatic analysis system 3 is in an off-line state. On the other hand, in a case of an on-line state, it is necessary to perform a reset operation, and thus it is determined whether the automatic analysis system 3 is in an on-line state or an off-line state (step 103). When it is determined that the automatic analysis system is in an on-line state, the reset of a region taking charge of a connection portion is performed (step 105). When it is determined that the automatic analysis system is in an off-line state, this process is passed. Next, normal reset is performed (step 107) and is then terminated.

Similarly, regarding the specimen processing system side, determination of whether being an on-line state or an off-line state (whether or not being in operation) is performed (step 102), and then respective reset processes are performed.

Finally, three branched reset processes are synchronized with each other to thereby terminate reset (step 109).

These settings can be performed by an operation unit, and an off-line state of the specimen processing system and an off-line state of the automatic analysis system can be set. A specific example will be described with reference to FIG. 6. FIG. 6 illustrates an example of a screen 201 required for setting.

Check boxes 202 and 203 are provided to set the specimen processing system 2 and the automatic analysis system 3 to be in an off-line state. In a case where the specimen processing system 2 is desired to set in an off-line state, the check box 202 is checked. In a case where the automatic analysis system 3 is desired to set in an off-line state, the check box 203 is checked. Thereafter, set contents are registered in a control system 4 by pressing an OK button 204.

In this manner, even in a system in which the specimen processing system and the automatic analysis system are connected to each other, it is possible to provide a highly efficient system which can separately control a pre-processing system region and an automatic analysis system region without physically separating the systems and which can be operated by designating an on-line state or an off-line state of each of the regions.

The control of a specimen 51 will be described below. Information regarding states (an off-line state or an on-line state) of the specimen processing system 2 and the automatic analysis system 3 is managed by the control system 4.

In a case where both the specimen processing system 2 and the automatic analysis system 3 are registered to be in an on-line state in the control system 4, the control system 4 performs control so as to transport the specimen between the specimen processing system 2 and the automatic analysis system 3. Specifically, two branch points (41, 43) that are present in the main transport line 11a are opened, and the specimen 51 transported in a direction of the arrow 21 by the main transport line 11a is transported to the automatic analysis system 3 as it is. In addition, two branch points (42, 44) that are present in the main transport line 11b are opened, and the specimen 51 transported in a direction of the arrow 22 by the main transport line 11b is transported to the specimen pre-processing system 3 as it is. Similarly, regarding the empty specimen rack 52, branch points 45 and 46 are opened, and control is performed so that the specimen 51 can move between the systems.

On the other hand, in a case where the specimen processing system 2 and the automatic analysis system 3 are respectively registered to be in an off-line state and an on-line state in the control system 4, the control system 4 controls the specimen 51 to be stayed within the automatic analysis system 3. Specifically, the branch point 42 of the main transport line 11b is closed, and the specimen 51 returned from the automatic analysis system 3 is avoided entering the pre-processing system connection region 31. The specimen 51 passes a bypass in a direction of an arrow 25, and then returns to the automatic analysis system 3 through the main transport line 11a. Similarly, regarding the empty specimen rack 52, the branch point 46 is closed, and the empty specimen rack 52 is controlled to return to the automatic analysis system 3 through the 12b.

In a case where, the specimen processing system 2 and the automatic analysis system 3 are respectively registered to be in an off-line state and an on-line state in the control system 4, the control system 4 controls the specimen 51 to be stayed within the specimen pre-processing system 2.

In the above-described invention, a description has been given of an example in which the pre-processing system and the automatic analysis system are respectively installed on the left side and the right side of the connection unit 1, but there is no essential difference even connections on the right and left sides are reversed.

Next, another example will be described with reference to FIGS. 7A and 7B. FIGS. 7A and 7B are diagrams illustrating the concept of division arrangement of the pre-processing system according to the invention. It is possible to increase variations in an layout of the system 300 by the position of the connection unit 1 according to the invention.

Here, the concept of a station required to describe variations in a layout of the system 300 will be briefly described. A reception station 210 refers to an aggregate of units constituted by, for example, an injection unit, a centrifugal unit, and an unplugging unit, and is in charge of a process of receiving a specimen. A dispensing station 220 refers to an aggregate constituted by, for example, a labeler unit and a dispensing unit, and is in charge of a process of dividing a specimen into small parts. A storage station 230 refers to an aggregate constituted by, for example, a plugging unit and a storage unit, and is in charge of a process of storing a specimen.

Regarding a layout of the system 300, in a system 301 in (a) of FIG. 7A, connection units (the right side unit is denoted by 1A, and the left side unit is denoted by 1B) are respectively disposed at both ends of each station (210, 220, 230). Thereby, a closed loop is configured in a transport path within each of the stations 210, 220, and 230, and the stations 210, 220, and 230 can be individually operated. In addition, the size of the system 300 can be freely determined by adjusting the length of the halfway transport path 330, and thus it is possible to construct a system with higher flexibility such as a layout being able to be designed in consideration of situations of an institution (an inspection room, a laboratory, or the like) to be introduced.

As an application mode, as in a system 302 in (b) of FIG. 7, the reception station 210 and the dispensing station 220 may be disposed in adjacent to each other, and only the storage station 230 may be disposed at a separate place. An inspection room in which a specimen storage place is separated from an analysis place is effective.

Alternatively, as in a system 303 in (c) of FIG. 7, the reception station 210 and the storage station 230 may be disposed in adjacent, and only the dispensing station 230 may be disposed at a separate place.

Alternatively, as in a system 304 in (d) of FIG. 7, analysis apparatuses (341, 342) may also be disposed between the reception station 210 and the dispensing station 220.

Furthermore, it is possible to further increase variations in a layout by forming the transport path 330 connecting the stations (210, 220, 230) or the automatic analysis apparatuses (341, 342) in an L shape.

Meanwhile, connection units 1A and 1B are disposed at ends on aside which is not connected to a transport path of a station (for example, the storage station 230 in (a) of FIG. 7A or the dispensing station 220 in (d) of FIG. 7B) which is located at the end of the system, but the connection units 1A and 1B are not necessarily essential. For example, in a case where the units disposed at ends of each station have already had a transport line structure for forming an end of a closed loop, these connection units may also be omitted.

REFERENCE SIGNS LIST

1 CONNECTION UNIT
1A CONNECTION UNIT (DISPOSED ON RIGHT SIDE)
1B CONNECTION UNIT (DISPOSED ON LEFT SIDE)
2 SPECIMEN PROCESSING SYSTEM
3 AUTOMATIC ANALYSIS SYSTEM
4 CONTROL SYSTEM
11 MAIN TRANSPORT LINE
11a MAIN TRANSPORT LINE (ADVANCING)
11b MAIN TRANSPORT LINE (RETURNING)
12 EMPTY RACK TRANSPORT LINE
12a EMPTY RACK TRANSPORT LINE (RETURNING)
12b EMPTY RACK TRANSPORT LINE (ADVANCING)
13 CONNECTION LINE
14 MAIN TRANSPORT LINE CONNECTION BYPASS
14a MAIN TRANSPORT LINE CONNECTION BYPASS (PRE-PROCESSING SYSTEM REGION)
14b MAIN TRANSPORT LINE CONNECTION BYPASS (AUTOMATIC ANALYSIS SYSTEM REGION)
15 EMPTY RACK LINE CONNECTION BYPASS
21 TO 27 ARROW
30 DASHED LINE INDICATING BOUNDARY OF EACH FUNCTION
31 PRE-PROCESSING SYSTEM CONNECTION REGION
33 AUTOMATIC ANALYSIS SYSTEM CONNECTION REGION
41 TO 46 BRANCH POINT
51 SPECIMEN
52 SPECIMEN RACK
61 CLOSED LOOP STRUCTURE OF EMPTY-RACK-ONLY TRANSPORT LINE FORMED IN CONJUNCTION WITH PRE-PROCESSING SYSTEM
62 CLOSED LOOP STRUCTURE OF MAIN TRANSPORT LINE FORMED IN CONJUNCTION WITH PRE-PROCESSING SYSTEM
63 CLOSED LOOP STRUCTURE OF EMPTY-RACK-ONLY TRANSPORT LINE FORMED IN CONJUNCTION WITH AUTOMATIC ANALYSIS SYSTEM
64 CLOSED LOOP STRUCTURE OF MAIN TRANSPORT LINE FORMED IN CONJUNCTION WITH AUTOMATIC ANALYSIS SYSTEM
71 ARROW INDICATING TRANSPORT DIRECTION OF SPECIMEN HOLDING RACK
72 ARROW INDICATING TRANSPORT DIRECTION OF EMPTY RACK
81 SPECIMEN HOLDING RACK DELIVERY LINE (WITHIN PRE-PROCESSING SYSTEM)
82 SPECIMEN HOLDING RACK RECEPTION LINE (WITHIN AUTOMATIC ANALYSIS SYSTEM)
83 SPECIMEN HOLDING RACK RECEPTION LINE (WITHIN PRE-PROCESSING SYSTEM)
84 SPECIMEN HOLDING RACK DELIVERY LINE (WITHIN AUTOMATIC ANALYSIS SYSTEM)
85 EMPTY RACK RECEPTION LINE (WITHIN PRE-PROCESSING SYSTEM)
86 EMPTY RACK DELIVERY LINE (WITHIN AUTOMATIC ANALYSIS SYSTEM)
87 EMPTY RACK DELIVERY LINE (WITHIN PRE-PROCESSING SYSTEM)
88 EMPTY RACK RECEPTION LINE (WITHIN AUTOMATIC ANALYSIS SYSTEM)
91 LEFT END OF ENTIRE SYSTEM
92 RIGHT END OF ENTIRE SYSTEM
101 START OF RESET
102 ON-LINE
103 ON-LINE
104 REGION RESET
105 REGION RESET
106 RESET
107 NORMAL RESET
108 NORMAL RESET
109 TERMINATION OF RESET
201 OFF-LINE SETTING WINDOW
202 CHECK BOX
203 CHECK BOX
204 OK BUTTON
210 RECEPTION STATION
220 DISPENSING STATION
230 STORAGE STATION
300 SYSTEM
301 TO 304 LAYOUT
341 TO 342 AUTOMATIC ANALYSIS APPARATUS
330 TRANSPORT PATH

The invention claimed is:
1. A connection unit disposed between first and second specimen processing systems to transport a specimen rack holding a specimen and an empty rack, the connection unit comprising:
a first transport line that transports the specimen rack in a first direction from the first specimen processing system toward the second specimen processing system;
a second transport line that transports the specimen rack in a second direction opposite to the first direction;
a first connection bypass that connects the first transport line and the second transport line to each other and transports the specimen rack in a third direction;
a second connection bypass that connects the first transport line and the second transport line to each other and transports the specimen rack in a fourth direction opposite to the third direction;
a first empty rack transport line that is disposed in a layer different from that of the first transport line and transports the empty rack in the first direction;

a second empty rack transport line that is disposed in the layer different from that of the first transport line that and transports the empty rack in the second direction;
a first empty rack connection bypass that connects the first empty rack transport line and the second empty rack transport line to each other and transports the empty rack in the third direction; and
a second empty rack connection bypass that connects the first empty rack transport line and the second empty rack transport line to each other and transports the empty rack in the fourth direction,
wherein the first specimen processing system, the first transport line, the second transport line, and the first connection bypass constitute a first loop structure,
wherein the second specimen processing system, the first transport line, the second transport line, and the second connection bypass constitute a second loop structure,
wherein the first specimen transport system, the first empty rack transport line, the second empty rack transport line, and the first empty rack connection bypass constitute a third loop structure,
wherein the second specimen transport system, the first empty rack transport line, the second empty rack transport line, and the second empty rack connection bypass constitute a fourth loop structure,
wherein the first transport line extends between the first loop structure and the second loop structure,
wherein the second transport line extends between the first loop structure and the second loop structure,
wherein the first empty rack transport line extends between the third loop structure and the fourth loop structure,
wherein the second empty rack transport line extends between the third loop structure and the fourth loop structure, and
wherein a connection line is disposed outside of the first loop structure and the third loop structure and connects the second loop structure with the fourth loop structure.

2. The connection unit according to claim 1, wherein the first specimen transport system is a specimen processing system, and the second specimen transport system is an analysis system.

3. The connection unit according to claim 1, wherein the first empty rack transport line and the second empty rack transport line are disposed between the first transport line and the second transport line.

4. The connection unit according to claim 1, further comprising:
a control unit that performs control so that the number of racks is not biased between regions by transporting a rack having a specimen mounted thereon between the first loop structure and the second loop structure and transporting an empty rack between the third loop structure and the fourth loop structure.

5. The connection unit according to claim 1, further comprising:
a branch mechanism that moves the specimen rack on the first transport line to the first connection bypass, and a branch mechanism that moves the specimen rack on the second transport line to the second connection bypass.

6. The specimen transport system according to claim 1, wherein, the control unit is further programmed to perform a reset process on the first loop structure and the third loop structure when only the first specimen processing system is set in the operable state, and to perform the reset process on the second loop structure and the fourth loop structure when only the second specimen processing system is set in the operable state.

7. The connection unit according to claim 1, further comprising:
a control unit that performs control so as to individually set the first loop structure or the second loop structure to be in an operation state or a pause state.

8. The connection unit according to claim 7, wherein the control unit switches operation conditions of the first loop structure and the second loop structure depending on whether the first specimen transport system and the second specimen transport system are in an off-line state or an on-line state.

9. The connection unit according to claim 1, wherein the connection unit is disposed between a plurality of stations having different functions.

10. The connection unit according to claim 9, further comprising:
a branch mechanism that moves the empty rack on the first empty rack transport line to the first empty rack connection bypass, and a branch mechanism that moves the empty rack on the second empty rack transport line to the second empty rack connection bypass.

11. A specimen transport system comprising:
a connection unit;
a first specimen processing system that transports a specimen rack holding a specimen to the connection unit;
a second specimen processing system that is operable separately from the first specimen processing system and receives the specimen rack from the connection unit; and
a control unit programmed to control the connection unit, the first specimen processing system, and the second specimen processing system such that each of the first specimen processing system or the second specimen processing system is separately set to be in an operation state or a pause state,
wherein the connection unit is disposed between the first specimen processing system and the second specimen processing system, and includes:
a first transport line that transports the specimen rack in a first direction from the first specimen processing system toward the second specimen processing system,
a second transport line that transports the specimen rack in a second direction opposite to the first direction,
a first connection bypass that connects the first transport line and the second transport line to each other and transports the specimen rack in a third direction,
a second connection bypass that connects the first transport line and the second transport line to each other and transports the specimen rack in a fourth direction opposite to the third direction,
a first empty rack transport line that is disposed in a layer different from that of the first transport line and transports the empty rack in the first direction,
a second empty rack transport line that is disposed in the layer different from that of the first transport line that and transports the empty rack in the second direction,
a first empty rack connection bypass that connects the first empty rack transport line and the second empty rack transport line to each other and transports the empty rack in the third direction, and a second empty rack connection bypass that connects the first empty rack transport line and the second empty rack transport line to each other and transports the empty rack in the fourth direction, wherein the first specimen processing system, the first transport line, the second transport line, and the first connection bypass constitute a first loop structure, wherein the second specimen processing system, the first transport line, the second transport line, and the second connection bypass constitute a second loop structure, wherein the first specimen transport system, the first empty rack transport line, the second empty rack transport line, and the first empty rack connection bypass constitute a third loop structure, wherein the second specimen transport system, the first empty rack transport line, the second empty rack transport line, and the second empty rack connection bypass constitute a fourth loop structure, wherein the first transport line extends between the first loop structure and the second loop structure, wherein the second transport line extends between the first loop structure and the second loop structure, wherein the first empty rack transport line extends between the third loop structure and the fourth loop structure, wherein the second empty rack transport line extends between the third loop structure and the fourth loop structure, and wherein a connection line is disposed outside of the first loop structure and the third loop structure, and connects the second loop structure with the fourth loop structure, and wherein the control unit is further programmed to control the only the first loop structure and the third loop structure when only the first specimen processing system is set in the operable state, and to control only the second loop structure and the fourth loop structure when only the second specimen processing system is set in the operable state.

* * * * *